United States Patent
Park et al.

(10) Patent No.: US 8,242,094 B2
(45) Date of Patent: Aug. 14, 2012

(54) SIRNA OF NF-KB P105 FOR INHIBITING CELL PROLIFERATION AND MIGRATION AND A COMPOSITION COMPRISING SAME

(75) Inventors: Myung-Ok Park, Seoul (KR); Choun-Ki Joo, Seoul (KR); Jun-Sub Choi, Yongin-shi (KR); Kyung-A Kim, Seoul (KR); Sung-Sik Bang, Suwon-si (KR)

(73) Assignee: Biopolymed, Inc. (KR)

( * ) Notice: Subject to any disclaimer, the term of this patent is extended or adjusted under 35 U.S.C. 154(b) by 132 days.

(21) Appl. No.: 12/674,244

(22) PCT Filed: Aug. 22, 2008

(86) PCT No.: PCT/KR2008/004922
§ 371 (c)(1),
(2), (4) Date: Feb. 19, 2010

(87) PCT Pub. No.: WO2009/025527
PCT Pub. Date: Feb. 26, 2009

(65) Prior Publication Data
US 2011/0280929 A1  Nov. 17, 2011

(30) Foreign Application Priority Data
Aug. 23, 2007 (KR) .................. 10-2007-0085155

(51) Int. Cl.
*A61K 31/70* (2006.01)
*C07H 21/02* (2006.01)
*C07H 21/04* (2006.01)

(52) U.S. Cl. ............. 514/44 A; 536/24.1; 536/24.5
(58) Field of Classification Search .......... 536/24.1, 536/24.5
See application file for complete search history.

(56) References Cited

U.S. PATENT DOCUMENTS
2005/0118625 A1* 6/2005 Mounts ............... 435/6

FOREIGN PATENT DOCUMENTS
KR  10-0825519 B1  4/2008
WO  WO 2004-009769 A2  1/2004

OTHER PUBLICATIONS
S. Akhtar (Gene Therapy, 2006 vol. 13:739 and 740).*
GenBank Accession No. NM_003998, Aug. 20, 2007.
Cancer Res. vol. 66(17): 8382-8388 (Kai Gao et al) Sep. 1, 2006.
Mol Cancer Res. vol. 4(2): 101-112 (Pei-Yun Chang et al) Feb. 2006.

* cited by examiner

*Primary Examiner* — Terra Cotta Gibbs
(74) *Attorney, Agent, or Firm* — John K. Park; Park Law Firm

(57) ABSTRACT

The present invention relates to a siRNA which targets mRNA of the NF-Kappa B p105 gene to cause its degradation by RNAi induction. In addition, the present invention provides a pharmaceutical composition for the treatment of diseases associated with aberrant cell proliferation and migration, comprising the siRNA and delivery vehicle capable of intracellular delivery of the same.

14 Claims, 3 Drawing Sheets

1. SiRNA sequence of NF-kappa B p105

1. GCCAAAGAAGGACATGATAAA  SEQ ID NO:1
2. TGGCAGGTATTTGACATATTA  SEQ ID NO:2
3. TCTGATGATTTACTAGCACAA  SEQ ID NO:3
4. ATCTGAAGCTGCAGCTGTATA  SEQ ID NO:4
6. GATCCTTCTTTGACTCATACA  SEQ ID NO:6
5. AGAAATTCCTGATCCAGACAA  SEQ ID NO:5
7. GCCTGAATCATTCTCGATTTA  SEQ ID NO:7
8. CTACGTTCCTATTGTCATTAA  SEQ ID NO:8
9. GGCTTCCTTTCTTGGTTCATA  SEQ ID NO:9
10. TGGTTACAATCATTGCTGAAA  SEQ ID NO:10

[Fig. 1]

1. SiRNA sequence of NF-kappa B p105

1. GCCAAAGAAGGACATGATAAA  SEQ ID NO:1
   2. TGGCAGGTATTTGACATATTA  SEQ ID NO:2
   3. TCTGATGATTTACTAGCACAA  SEQ ID NO:3
   4. ATCTCAAGCTGCACCTGTATA  SEQ ID NO:4
   6. GATCCTTCTTTGACTCATACA  SEQ ID NO:6
   5. AGAAATTCCTGATCCAGACAA  SEQ ID NO:5
   7. GCCTGAATCATTCTCGATTTA  SEQ ID NO:7
   8. CTACGTTCCTATTGTCATTAA  SEQ ID NO:8
   9. GGCTTCCTTTCTTGGTTCATA  SEQ ID NO:9
   10. TGGTTACAATCATTGCTGAAA  SEQ ID NO:10

[Fig. 2]

2. Inhibition of NF-kB P105 and P50 expression of lens epithelial cells

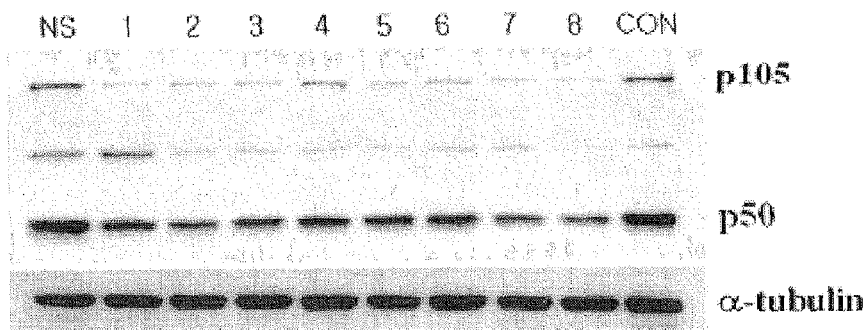

[Fig. 3]
Inhibition of migration in SiRNA treated B3 cells
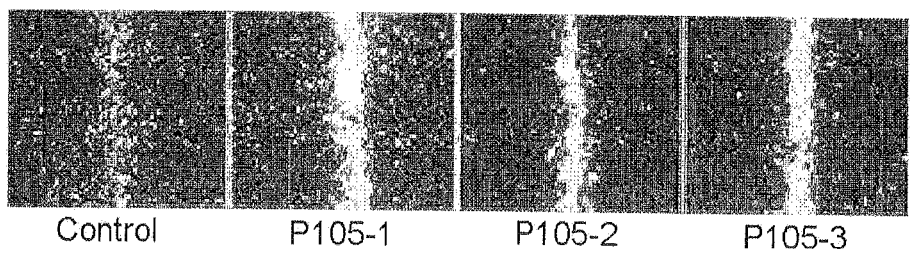
Control     P105-1     P105-2     P105-3
[Fig. 4]
A. Inhibition of migration in SiRNA treated B3 cells
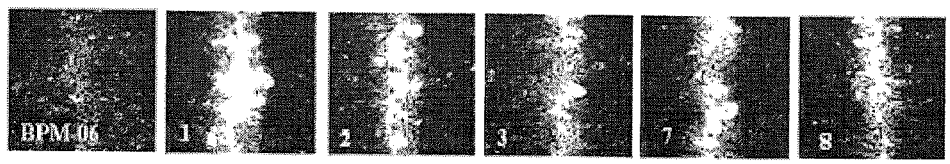
B. Inhibition of migration in SiRNA treated B3 cells
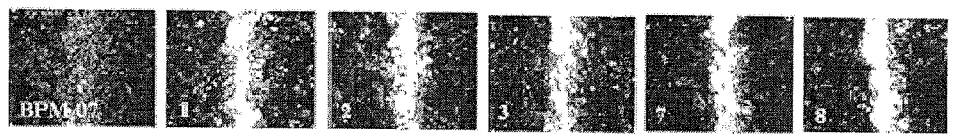
[Fig. 5]
Inhibition of mitgration in SiRNA treated H1299 cells
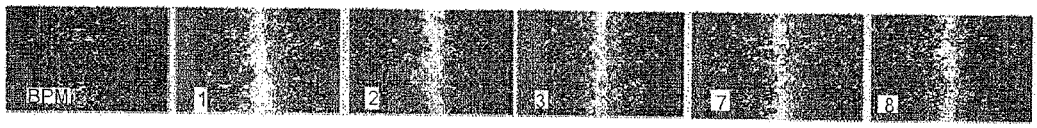

[Fig. 6]
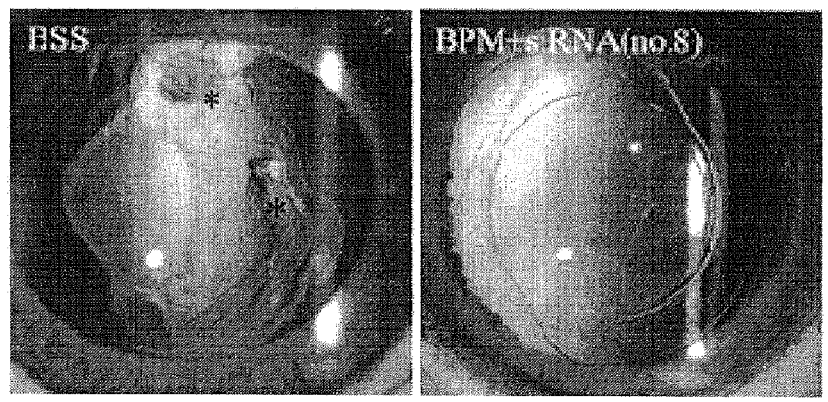

SIRNA OF NF-KB P105 FOR INHIBITING CELL PROLIFERATION AND MIGRATION AND A COMPOSITION COMPRISING SAME

TECHNICAL FIELD

The present invention relates to a siRNA of NF-kappaB p105 for inhibiting cell proliferation and migration, and to a pharmaceutical composition comprising a delivery vehicle capable of intracellular delivery of the same.

BACKGROUND ART

RNAi (RNA interference) is a phenomenon capable of inducing the selective degradation of target gene mRNA so as to silence the target gene expression by introducing into cells a double-stranded RNA that comprises a sense RNA having the sequence homologous to the target gene mRNA and an antisense RNA having the sequence complementary to the sense RNA. RNAi, because of its capability to selectively silence the target gene expression, has received considerable attention as a simple gene knock-down method that replaces the conventional gene disruption method relying on the tedious, inefficient homologous recombination. The above-mentioned RNAi was originally discovered in nematodes (Nature, 391, 806-811, 1998). Thereafter, it is also observed in various organisms including plants, round worms, Drosophila, and protozoa (Genes Dev. 15, 485-490, 2001). Recently, it was reported that RNAi can be induced also in mammalian cells by transducing the cells with short dsRNAs of 21 or 22 nucleotide long having a single-stranded 2 or 3 nucleotide of 3'-overhang terminus in place of long dsRNAs as those used in other organisms (Nature 411, 494-498, 2001).

An RNAi-inducing entity, siRNA (small interference RNA) is a short, double-helix RNA strand consisting of about 19 to 23 nucleotides, which can suppress expression of a targeted mRNA being related to a disease and having complementary base sequence to the siRNA. However, since siRNA has very low stability and is quickly degraded in vivo, its therapeutic efficiency deteriorates quickly. Even though the dose of expensive siRNA can be increased, the anionic nature of siRNA hinders it from permeating a cell membrane with negative charge, leading to low levels of siRNA transfer into intracellular compartments (Chemical and Engineering News December 22, 32-36, 2003). In addition, the linkage of a ribose sugar in siRNA is chemically very unstable, and thus the majority of siRNA has a half-life of about 30 minutes in vivo and is quickly degraded.

Accordingly, there is a need to develop a technology for the preparation of a novel delivery system that facilitates intracellular transfer of siRNA as a gene-based therapeutic agent. In general, siRNA can be administered to a subject as a recombinant plasmid or a viral vector which expresses the siRNA.

Alternatively, siRNA can be administered to a subject as a naked siRNA in conjunction with a delivery reagent such as Mirus Transit TKO lipophilic reagent, lipofectin, lipofectamine, cellfectin, cationic phospholipid nanoparticles, polycations, liposomes, etc. To improve in vivo stability of siRNA, a biocompatible polymer such as a polyethylene glycol is also conjugated to siRNA to increase the cellular uptake of siRNA. Kataoka et. al. prepared a PEG-siRNA conjugate to improve the low stability against the enzymatic degradation of siRNA and low permeability across the cell membrane, and they developed it as a siRNA delivery system for tumor targeting (J. Am. Chem. Soc. 127, 1624, 2005).

Cationic phospholipid nanoparticles are disclosed in U.S. Pat. No. 5,858,784 and US Patent Publication NO. 20060008910AI, in which cationic lipids are mixed with phospholipids in a predetermined ratio to prepare particles such as cationic liposome, the particles are mixed with nucleic acid to prepare a complex of cationic phospholipids particles and nucleic acid, and the complex is introduced into a cell line to improve gene expression. Cationic polymers have been also studied as a gene delivery vehicle, which are disclosed as follows: DEAE dextran, polylysine having repeating lysine units, and polyethyleneimine having repeating ethyleneimine units, polyamidoamine (U.S. Pat. No. 6,020,457), poly-amino-ester (US Patent Publication NO. 20040071654A1), and a biodegradable cationic copolymer (US patent Publication NO. 20060093674A1).

As a gene delivery vehicle, the synthetic polymers are advantageous in that they are easily prepared, not limited by the size of gene to be introduced, generate fewer side effects that may be induced by immunogenic viral surface protein upon repeated administration, cause no safety problems due to viral genes, and require lower production cost in a commercial process, as compared to viral vectors including lentiviral, adenoviral and retroviral vectors. However, there are drawbacks in that the delivery systems using such cationic polymers have lower transfection efficiency as compared to viral vectors that are effectively transferred via cell surface receptors, and might induce cytoxicity (J. Control. Release 114, 100-109, 2006). Another drawback of the cationic polymer mediated gene transfer is that it does not greatly prolong the half life of the gene in blood (Gene Ther. 8, 1857-1892).

For the purpose of improving the problems, recent studies have been made on a polymer conjugate of polyethylene glycol and chitosan having excellent biocompatibility and industrial availability as a delivery system (U.S. Pat. No. 6,730,742). However, there is a limitation that only the conjugation does not significantly improve the gene transfer efficiency. Accordingly, the present inventors prepared a double conjugate by linking polyamine to chitosan or a triple conjugate by additionally linking polyethylene glycol to the double conjugate, as disclosed in Korean Patent Application NO. 10-2007-0001715. They found that the conjugates had lower cytotoxicity, higher transfer efficiency, and longer retention time in blood than the known gene delivery systems.

DISCLOSURE

Technical Problem

The present inventors have prepared a siRNA of NF-kappaB p105 capable of inhibiting aberrant cell proliferation and migration, and determined the optimum conditions for maximum transfer efficiency thereof without cytotoxicity, and thus developed a pharmaceutical composition that is advantageous in terms of cost and safety, and is applicable to a wide range of fields from cataract to cancer treatment, thereby completing the present invention.

Technical Solution

It is an object of the present invention to provide a siRNA of NF-kappaB p105 capable of inhibiting aberrant cell proliferation and migration.

It is another object of the present invention to provide a delivery vehicle capable of intracellular delivery of said siRNA without cytotoxicity, and an intracellular delivery method for the siRNA using the delivery vehicle.

It is still another object of the present invention to provide a pharmaceutical composition for the treatment of diseases associated with aberrant cell proliferation and migration, comprising a complex of said delivery vehicle and siRNA.

Advantageous Effects

The composition comprising the siRNA of NF-kappaB p105 or comprising the siRNA and a delivery vehicle capable of intracellular delivery of the siRNA according to the present invention can inhibit abnormal cell proliferation and migration. Thus, the composition of the present invention can advantageously be used for the prevention of abnormal cell proliferation induced in inflammation or immune responses, or cancer cell proliferation, in particular, for the treatment of after-cataract. In addition, when the chitosan-based polymer conjugate according to the present invention is preferably used as a delivery vehicle, the composition of the present invention can be used as a preferred therapeutic composition having higher transfer efficiency and lower cytotoxicity.

DESCRIPTION OF DRAWINGS

FIG. 1 illustrates the siRNA sequences inhibiting expression of NF-kappaB p105, prepared according to the present invention, which is shown in the "Sequence Listing";

FIG. 2 is the result of Western blot, in which the inhibitory effect of the siRNA of Example 1-1 on NF-kappaB p105 expression was analyzed in human lens epithelial cells;

FIG. 3 illustrates the inhibitory effect of the siRNA according to the present invention on cell proliferation and migration, in which the siRNAs were transfected into B3 cells by using lipofectamine;

FIG. 4-A illustrates the inhibitory effect of the siRNA according to the present invention on cell proliferation and migration, in which the siRNAs were transfected into B3 cells by using the polyethylene glycol-chitosan-polyamine conjugate according to Example 2-4, and FIG. 4-B illustrates the inhibitory effect of the siRNA according to the present invention on cell proliferation and migration, in which the siRNAs were transfected into B3 cells by using the polyethylene glycol-chitosan-polyamine conjugate according to Example 2-5;

FIG. 5 illustrates the inhibitory effect of the siRNA according to the present invention on cell proliferation and migration, in which the siRNAs were transfected into human lung cancer cells (H1299) by using the polyethylene glycol-chitosan-polyamine conjugate according to Example 2-4; and FIG. 6 illustrates the inhibitory effect of siRNA-BPM polymer on after-cataract, which was observed using a direct ophthalmoscope.

BEST MODE

In accordance with an aspect, the present invention provides a siRNA of NF-kappaB p105, which inhibits aberrant cell proliferation and migration.

NF-kappaB is a ubiquitous transcription factor that is needed for cell proliferation, and extensively exploited by inflammatory and immune cells. However, inhibition of NF-kappaB may induce damage to cell survival. Thus, a siRNA of the NF-kappaB p50 precursor, p105 was prepared, and its inhibitory activity on protein expression was studied in the present invention.

In a preferred embodiment of the present invention, the cDNA sequence for NF-kappaB p105 was obtained through searching NCBI database, and siRNAs were prepared using the cDNA sequence. The prepared siRNAs were evaluated for target specificity by performing a NCBI nucleotide BLAST search, so as to obtain a siRNA of NF-kappaB p105 comprising a short double-stranded RNA which consists of about 16 to 25 nucleotides, preferably about 17 to 22 nucleotides, and more preferably about 19 to 21 nucleotides.

To confirm the inhibitory effect of the specific siRNAs on cell proliferation, B3 human lens epithelial cell line (ATCC CRL-112421), in which cell proliferation and migration were artificially induced, and H1299 human lung cancer cell line (ATCC CRM-5803) were cultured in the media containing the siRNA (100 nM), and Western blot analysis was performed to observe the expression patterns of NF-kappaB p105 and p50 (see FIG. 2). In addition, based on the results of Western blot, 10 types of siRNAs inhibiting NF-kappaB p105 expression were finally selected, base sequences of which were shown in FIG. 1 and SEQ ID NOs. 1 to 10. Significant inhibition of cell proliferation and migration was observed in the siRNA treated cells, as compared to a control group (see FIGS. 3 to 5).

In accordance with another aspect of the present invention, the present invention provides a delivery vehicle capable of intracellular delivery of the siRNA without cytotoxicity, and an intracellular delivery method for the siRNA using the delivery vehicle.

The siRNA according to the present invention may be easily delivered into cells using any delivery vehicle known to those skilled in the art. That is, the siRNA according to the present invention can be delivered in conjunction with a delivery reagent such as Mirus Transit TKO lipophilic reagent, lipofectin, lipofectamine, cellfectin, cationic phospholipid nanoparticles, polycations, liposomes, etc., delivered as a recombinant plasmid or viral vector which expresses the siRNA, or delivered by conjugation with biocompatible polymer derivatives such as polyethylene glycol. Any delivery vehicle may be used, as long as it is capable of intracellular delivery of the siRNA according to the present invention.

In a preferred embodiment, the siRNA may be transferred by using a double conjugate of chitosan and polyamine or a chitosan-based triple conjugate prepared by covalently linking polyamine and polyethylene glycol to chitosan, as disclosed in Korean Patent Application NO. 10-2007-0001715 applied by the present inventors.

The chitosan to be used for the preparation of the chitosan-based polymer conjugates is derived from chitin through N-deacetylation, and may be derived from outer coat of insects and Crustacea or may be also commercially available. Chitosans having different molecular weights may be used in the present invention, and in an embodiment of the present invention, chitosan having a molecular weight of fw 50,000 to 150,000 (Fluka, Swiss) is used to prepare the chitosan-based cationic polymer conjugate.

In order to prepare the chitosan-based polymer conjugate, any polyamine may used, as long as it has two or more amino groups in its molecule. Polyamine is commercially available or may be prepared by a known method in the related art.

In a specific embodiment, the chitosan-based polymer conjugates were prepared by using various polyamines having a molecular weight of 500 to 300,000. In particular, the present inventor used poly-L-arginine having a molecular weight of 15,000 to 70,000 or having a molecular weight of 70,000 or more (Sigma, USA), and poly-L-lysine having a molecular weight of 9,200 (Sigma, USA) to prepare the chitosan-polyamine conjugates.

In the case of linking polyethylene glycol (PEG) to the chitosan-based cationic polymer conjugate of the present invention, polyethylene glycol preferably has an average molecular weight of about 300 to 100,000 daltons, and more preferably 1,000 to 20,000 daltons. Activation of the polyethylene glycol may be achieved by converting any one of the terminal groups of the polyethylene glycol into a reactive group or moiety to bind with chitosan. The product by said modification is referred to as an "activated biocompatible polymer" or "activated polyethylene glycol". In the present invention, the amino or hydroxy group of chitosan is protected with a protecting material such as phthalic anhydride, and then the activated polyethylene glycol is linked to a specific site of said chitosan.

Upon preparation of the conjugates, a molar ratio (%) of chitosan and polyamine is 1:1 to 1:10, and preferably 1:1 to 1:2. Upon additional binding reaction of polyethylene glycol, a molar ratio (%) of chitosan and polyethylene glycol is 1:1 to 1:50, and preferably 1:5 to 1:25.

The present inventor performed electrophoresis to confirm complex formation of siRNA and the double conjugate of chitosan and polyamine or the triple conjugate of polyethylene glycol-chitosan-polyamine in Korean Patent Application NO. 10-2007-0001715. As a result, it was observed that as the amount of the chitosan-based polymer conjugate increased to increase the amount of the complex, the amount of siRNA, which is not involved in the complex formation and thus tends to move on the electrophorosis gel, decreased. Therefore, the chitosan-based polymer conjugate can be used as a delivery vehicle for the siRNA according to the present invention.

Accordingly, the human lens epithelial cell line (B3 cell line), where cell proliferation and migration were artificially induced, was treated with the siRNA according to the present invention in conjunction with the known lipofectamine or with the chitosan-based polymer conjugate according to the prior application of the present inventor. In the cells treated with each of the delivery vehicles, significant inhibition of cell proliferation and migration was observed, as compared to a control group, which is not treated with the siRNA according to the present invention (see FIGS. 3 and 4). In addition, when the human lung cancer cell line (H1299) was treated with a complex of the siRNA and chitosan-based polymer conjugate, significant inhibition of cell proliferation and migration was also observed, as compared to a control group, which is treated with only the chitosan-based polymer conjugate (without siRNA) (see FIG. 5).

Furthermore, no cytotoxicity was observed in the group treated with the complex of the siRNA and chitosan-based polymer conjugate.

In accordance with still another aspect, the present invention provides a pharmaceutical composition for the treatment of diseases associated with aberrant cell proliferation and migration, comprising the siRNA according to the present invention or the complex of said siRNA and a delivery vehicle. In a preferred embodiment, the delivery vehicle is preferably the chitosan-based polymer conjugate according to the prior application of the present inventor, but is not limited thereto, and may be readily selected from various gene delivery vehicles known to those skilled in the art. Examples thereof may include a recombinant plasmid or a recombinant viral vector, a siRNA delivery reagent such as polycations and liposomes, and a biocompatible polymer such as polyethylene glycol, but are not limited thereto.

In the present invention, "diseases associated with aberrant cell proliferation and migration" may include tumor diseases, inflammatory diseases, after cataract, etc., and tumor diseases may particularly include cancer, preferably breast cancer, lung cancer, head and neck cancer, brain cancer, abdominal cancer, colon cancer, esophageal cancer, gastric cancer, liver cancer, tongue cancer, neuroblastoma, osteosarcoma, ovarian cancer, pancreatic cancer, prostate cancer, wilm's tumor, retinoblastoma, multiple myeloma, skin cancer, lymphoma, hematologic cancer, etc., and are not limited thereto. As described above, in Example 3-2 of the present invention, when the siRNA according to the present invention was transferred into the human lung cancer cell line, inhibition of cell proliferation and migration was observed.

A cataract is a clouding that develops in the normally clear lens of the eye, which prevents the lens from properly focusing light on the retina. After-cataract is posterior capsular opacity (PCO) following cataract surgery, and its incidence rate is 20 to 25%, and is higher in patients younger than 50 years of age after cataract surgery, not in the elderly. After-cataract is a disease associated with abnormal proliferation of the residual lens epithelial cells after cataract surgery. Thus, it is required to prevent after-cataract following cataract surgery. In Example 3-1 of the present invention, the siRNA according to the present invention was transferred into the human lens epithelial cell where cell proliferation and migration were artificially induced. As a result, it was observed that the siRNA according to the present invention inhibited the cell proliferation and migration.

In a preferred embodiment, the pharmaceutical composition comprises a complex of the chitosan-based polymer conjugate and the siRNA according to the present invention, in which the chitosan-based polymer conjugate is a double conjugate of "chitosan-polyamine" or a triple conjugate of "polyethylene glycol-chitosan-polyamine". In the present Examples, chitosan-based polymer conjugates were prepared by using chitosan and polyethylene glycol, each of which has a predetermined molecular weight, and polyamines consisting of specific amino acids, and then were used for complex formation with the siRNA according to the present invention. However, the chitosan-based polymer conjugate is not limited thereto, and may include various types of polymer conjugates as a delivery vehicle, as described in Korean Patent Application NO. 10-2007-001715. Accordingly, the disclosure thereof is incorporated herein by reference in its entirety.

The pharmaceutical composition of the present invention may be administered with a pharmaceutically acceptable carrier. For oral administration, the pharmaceutical composition may further include a binder, a lubricant, a disintegrator, an excipient, a solubilizer, a dispersing agent, a stabilizer, a suspending agent, a coloring agent, a perfume or the like, in addition to the active ingredients. For injectable preparations, the pharmaceutical composition may be used in a mixture with a buffering agent, a preserving agent, an analgesic, a solubilizer, an isotonic agent, a stabilizer or the like. For preparations for topical administration, the pharmaceutically acceptable carrier may include a base, an excipient, a lubricant, and a preserving agent. The composition of the present invention may be formulated into a variety of dosage forms in combination with the aforementioned pharmaceutically acceptable carriers. For example, for oral administration, the composition may be formulated into tablets, troches, capsules, elixirs, suspensions, syrups or wafers. For injectable preparations, the pharmaceutical composition may be formulated into an ampule as a single-dose dosage form or a unit dosage form, such as a multidose container. The pharmaceutical composition may be also formulated into solutions, suspensions, tablets, pills, capsules and sustained released preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the formulations may further include fillers, anti-coagulating agents, lubricants, humectants, perfumes, and antiseptics.

The pharmaceutical composition of the present invention may be administered via any of the common routes, as long as it is able to reach a desired tissue. A variety of administration modes are contemplated, including orally, intraperitoneally, intravenously, intramuscularly, subcutaneously, intradermally, topically, intranasally, intrapulmonarily and intrarectally, but the present invention is not limited to these exemplified administration modes.

An effective dose of the siRNA of NF-kappaB p105 contained in the pharmaceutical composition of the present invention may be determined by several related factors including the types of diseases to be treated, administration routes, the patient's age, gender, weight and severity of the illness, as well as by the types of the drug as an active ingredient. In the pharmaceutical composition of the present invention, siRNA may be preferably used in an amount of 0.1-500 pmole per weight (gram) for systemic or topical administration, and plasmid DNA may be used in an amount of 0.1-1000 ug per weight (gram) for systemic or topical administration.

MODE FOR INVENTION

Hereinafter, the present invention will be described in detail with reference to Examples. However, these Examples are for illustrative purposes only, and the invention is not intended to be limited by these Examples.

EXAMPLE

1. Preparation of siRNA and Inhibition of NF-KappaB Expression 1-1. Preparation of siRNA The cDNA sequence for NF-kappaB p105 was obtained through searching NCBI database, and siRNAs were prepared using the cDNA sequence. The prepared siRNAs were evaluated for target specificity to the NF-KappaB p105 gene by performing a NCBI nucleotide BLAST search.

1-2. Cell Culture and Final Selection of siRNAs Inhibiting NF-KappaB Expression

The human lens epithelial cell (B3 cell, ATCC CRL-112421, $5 \times 10^4$ cells/well) and human lung cancer cell line (H1229, ATCC CRM-5803, $1.3 \times 10^5$ cells/well) were cultured in DMEM media supplemented with 10% FBS, and grown to 85% confluency in culture plates. Then, to induce cell proliferation and migration, the cell layer was damaged.

Then, B3 and H1229 cell lines were placed in a fresh media, OPTI-MEM containing siRNA (100 nM) selected in Example 1-1. After 24 hrs, inhibitory effects on cell proliferation and migration were examined. Western blot analysis was performed to confirm the inhibitory effect on NF-KappaB p105 (FIG. 2). Based on the results, inhibition of p105 expression and p50 expression were examined to finally select 10 siRNAs, which are represented by SEQ ID NOs. 1 to 10 and shown in FIG. 1.

2. Preparation of Chitosan Based Polymer Conjugates (mPEG-chitosan-poly-L-arginine Conjugates)

2-1. Preparation of mPEG2K-COCH($CH_3$)Cl mPEG2K-OH (0.5 g, 0.25 mmol, IDB, Korea), 4-dimethylaminopyridine (DMAP; 91.6 mg, 0.75 mmol, fw122.17), and triethylamine (TEA; 0.070 ml, 0.5 mmol, fw 101.19) were dissolved in 12 ml of dichloromethane (DCM), and then slowly added to a solution of 2-chloropropionyl chloride (0.12 ml, 1.25 mmol, fw126.97) dissolved in 3 ml of DCM at 0° C. under nitrogen gas, and then the reaction temperature was raised from 0° C. to room temperature, followed by stirring for 24 hrs. The reaction was confirmed by TLC, and then the reaction mixture was extracted with DCM, and washed with water and brine. A DCM layer was dried over $MgSO_4$, and filtered. The reaction mixture was concentrated under reduced pressure, and precipitated in diethyl ether, filtered, and purified. The resultant was recrystallized in ethyl acetate, filtered, and purified. The structure of the title compound was confirmed by 500 MHz 1 H-NMR.

2-2. Preparation of Phthaloyl Chitosan (phth-chitosan)

A chitosan (Chitosan, Sigma, 500 mg, 3.1 mmol of pyranose unit fw161) and phthalic anhydride (1.38 g, 9.32 mmol, fw 148.12) were dissolved in 10 ml of dimethylformamide (DMF), and the solution was heated to 130° C. under nitrogen gas, followed by stirring for 7 hrs. The reactant was cooled to room temperature, and the precipitate was washed with ice water, and filtered. The resulting solid was purified with ethanol by soxhlet extraction. The resulting solid was dried under vacuum at 50° C. to give a phth-chitosan having a protected amine group of chitosan.

2-3. Preparation of 10 mol % PEGylated 5'-mPEG2K-Chitosan

A phth-chitosan (70 mg, 0.24 mmol of protected pyranose unit fw291) prepared in Example 2-2 was dissolved in 1 ml of pyridine, and the solution was mixed with a solution of mPEG2K-COCH($CH_3$)Cl (72.2 mg, 36.1 µmol) prepared in Example 2-1 in 2 ml of DMF. The mixture was heated to 100° C. under nitrogen gas, followed by stirring for 24 hrs. The reactant was cooled to room temperature, and precipitated in ethanol. The resultant was washed with ethanol and ether, and filtered. The resulting solid 5'-mPEG2K-chitosan (phth), in which 5'C hydroxy group of chitosan was conjugated with PEG, was dried under vacuum. 50 mg of 5'-mPEG2K-chitosan(phth) was dissolved in 10 ml of hydrazine monohydrate ($H_2NNH_2H_2O$), and the solution was refluxed under nitrogen gas at 130° C., while stirring for 24 hrs. The reactant was cooled to room temperature. The precipitate was purified, and mixed with 10 ml of 0.1 M NaOH(aq), followed by stirring at room temperature for 16 hrs. The pH of the mixture was adjusted to 10 with 50 mM HCl(aq) by dialysis, and freeze-dried to give a compound 5'-mPEG2K-chitosan. The compound was confirmed by 500 MHz 1H-NMR.

2-4. 10% 5'-mPEG2k-chitosan-poly-L-arginine (fw 15,000~70,000)

2 mg of 5'-mPEG2K-chitosan prepared in Example 2-3 was dissolved in 1 ml of 50 mM MES buffer solution (pH 4.0), and then mixed with PLR (0.7 mg, $0.2 \times 10^{-7}$ mol, fw 15,000~70,000), EDAC (383.4 ug, $0.2 \times 10^{-5}$ mol, fw 191.7), and Sulfo-NHS (434.28 ug, $0.2 \times 10^{-5}$ mol, fw 217.14), followed by stirring at room temperature for 24 hrs. The mixture was purified using a centrifugal filter (MWCO 30k), and then freeze-dried to give a 5'-mPEG2k-chitosan-poly-L-arginine (fw 15,000~70,000) conjugate.

2-5. 10% 5'-mPEG2k-chitosan-poly-L-arginine (fw 70,000)

2 mg of 5'-mPEG2K-chitosan prepared in Example 2-3 was dissolved in 1 ml of 50 mM MES buffer solution (pH 4.0), and then mixed with PLR (1.4 mg, $0.2 \times 10^{-7}$ mol, fw 70,000), EDAC (383.4 ug, $0.2 \times 10^{-5}$ mol, fw 191.7), and Sulfo-NHS (434.28 ug, $0.2 \times 10^{-5}$ mol, fw 217.14), followed by stirring at room temperature for 24 hrs. The mixture was purified using a centrifugal filter (MWCO 30 k), and then freeze-dried to give a 5'-mPEG2k-chitosan-poly-L-arginine (fw 70,000) conjugate.

3. Inhibitory Effect of NF-kappaB p105 siRNA on Cell Proliferation and Migration 3-1. Inhibitory Effect of NF-KappaB p105 siRNA on Cell Proliferation and Migration in Human Lens Epithelial Cell The human lens epithelial cells (B3 cell), of which proliferation was induced as in Example 1-2, were transfected with the siRNA of NF-KappaB p105 in conjunction with lipofectamine (siRNA 100 nM+lipofectamine 6 µl) (FIG. 3) or with a chitosan-based polymer conjugate (siRNA 100 nM+chitosan-based polymer conjugate 10 µg) according to Example 2-4 (FIG. 4A) or Example 2-5 (FIG. 4B). After 24 hrs, the damage recovery and cell migration were examined (FIG. 4).

As shown in FIGS. 3 and 4, no empty area was observed due to cell migration, in the control group treated with only the lipofectamine or chitosan-based polymer conjugate (1 µg/µl) (without siRNA), but inhibition of cell proliferation and migration was observed in the siRNA treated cells. As shown in FIG. 3, when B3 cells were transfected with 10 siRNAs selected in Example 1-2 in conjunction with lipofectamine, the inhibitory effects on cell proliferation and migration were notably observed in the cells treated with the siRNAs represented by SEQ ID NOs. 1, 2 and 8. As shown in FIGS. 4A and 4B, when B3 cells were transfected with 10 siRNAs selected in Example 1-2 in conjunction with the chitosan-based polymer conjugates according to Examples 2-4 and 2-5, the inhibitory effects on cell proliferation and migration were notably observed in the cells treated with the siRNAs represented by SEQ ID NOs. 1, 2, 3, 7 and 8. Consequently, it can be seen that the siRNAs according to the present invention inhibit abnormal proliferation and migration of human lens epithelial cell. In particular, the chitosan-based polymer conjugates prepared by the present inventor showed excellent intracellular transfection efficiency of the siRNAs, as compared to the known lipofectamine. In addition, when the chitosan-based polymer conjugates were used as a delivery vehicle, no cytotoxicity was observed.

3-2. Inhibitory Effect of NF-KappaB p105 siRNA on Cell Proliferation and Migration in Human Lung Cancer Cell Inhibitory effect of NF-KappaB p105 siRNA according to the present invention on cell proliferation and migration was confirmed in human lung cancer cell (H1229, ATCC CRM-5803, $1.3 \times 10^5$ cells/well) as in Example 1-2. The human lung cancer cells (H1229) were transfected with a complex of the siRNA according to the present invention and the polyethylene glycol-chitosan-polyamine conjugate prepared in Example 2-4 (siRNA 100 nM+chitosan-based polymer conjugate 10 µg). After 24 hrs, damage recovery and cell migration were examined. As shown in FIG. 5, no empty area was observed due to cell migration, in the control group treated with only the chitosan-based polymer conjugate (1 µg/µl) (without siRNA), but inhibition of cell proliferation and migration was observed in the siRNA treated cells. Consequently, it can be seen that the siRNAs according to the present invention can be used for the treatment of diseases associated with aberrant cell proliferation and migration, in particular, cancer. No cytotoxicity was also observed.

4. Effect of NF-kappaB p105 siRNA on Cataract in Rabbits 4-1. Cataract Surgery in Rabbits Rabbits were used as an experimental animal, and all procedures were performed in accordance with the Association for Research in Vision and Ophthalmology Statement for the use of animals in Ophthalmic and Vision Research.

After repeated administration of a mydriatic agent to the eye, the rabbits were anesthetized by intramuscular injection with 5 mg/kg of 0.1% chloral hydrate and xylazine hydrochloride, and the periocular area was disinfected with povidone-iodine. Then, a clear corneal incision was made with a 3.0-mm keratome and side port was made with a 1-mm knife. The viscoelastic solution was injected into the anterior chamber. A small linear anterior capsulotomy (5 mm in diameter) was performed, and hydrodissection was performed using a balanced salt solution. The lens nucleus and cortex were removed by endocapsular phacoemulsification, mainly irrigation and aspiration. The viscoelastic material was injected into the anterior chamber, and the size of clear corneal incision was increased to 3.2 mm. Then, the viscoelastic material was injected into lens sac, and three-piece silicone IOL was implanted. After removing viscoelastic material using an aspirator, the mixture (0.1 ml) of NF-kappaB p105 siRNA of SEQ ID NO. 8 (100 pmoles) and BPMpolymer (10 ug) was injected into the anterior chamber. Two minutes after injection, the corneal incision was sutured with 10-0 nylon.

4-2. Postoperative Observation

In order to prevent inflammation and infection after the surgery, a 0.3% topical ofloxacin ophthalmic solution was applied to both eyes four times a day until enucleation.

At 1 month after the surgery, the posterior capsule was exposed under mydriasis, and occurrence of after-cataract was examined using a direct ophthalmoscope.

At 1 month after the surgery, the inhibitory effect on after-cataract was examined in the BSS control group and the group treated with the siRNA of SEQ ID NO. 8. In the BSS control group, posterior capsular opacity was significantly developed in artificial intraocular lens. However, posterior capsular opacity was inhibited in the siRNA-treated group (FIG. 6).

INDUSTRIAL APPLICABILITY

The composition comprising the siRNA of NF-kappaB p105 or a delivery vehicle capable of intracellular delivery of the siRNA according to the present invention can inhibit abnormal cell proliferation and migration. Thus, the composition of the present invention can be used for the prevention of abnormal cell proliferation induced in inflammation or immune responses, or cancer cell proliferation, in particular, for the treatment of after-cataract. In addition, when the chitosan-based polymer conjugate according to the present invention is preferably used as a delivery vehicle, the composition of the present invention can be used as a preferred therapeutic composition having higher transfer efficiency and lower cytotoxicity.

The invention claimed is

1. An siRNA of NF-kappaB p105, represented by SEQ ID NO. 8.

2. A complex of the siRNA according to claim 1 and a cationic polymer.

3. The complex according to claim 2, wherein the cationic polymer is a Mirus Transit TKO lipophilic reagent, lipofectin, lipofectamine, cellfectin, or liposome.

4. The complex according to claim 2, wherein the cationic polymer is a chitosan-polyamine or polyethylene glycol-chitosan-polyamine conjugate.

5. The complex according to claim 4, wherein the polyamine is polyarginine or polylysine.

6. A composition for the treatment of diseases associated with aberrant cell proliferation or migration, comprising the siRNA according to claim 1, wherein the disease associated with aberrant cell proliferation or migration is selected from the group consisting of inflammatory diseases, tumors and after-cataract.

7. The composition according to claim 6, further comprising an intracellular delivery vehicle.

8. The composition according to claim 7, wherein the delivery vehicle is a recombinant plasmid or viral vector.

9. The composition according to claim 7, wherein the delivery vehicle is a Mirus Transit TKO lipophilic reagent, lipofectin, lipofectamine, cellfectin, cationic phospholipid nanoparticle, polycation, or liposome.

10. The composition according to claim 7, wherein the delivery vehicle is polyethylene glycol (PEG).

11. The composition according to claim 7, wherein the delivery vehicle is a chitosan-polyamine or polyethylene glycol-chitosan-polyamine conjugate.

12. The composition according to claim 6, wherein the disease is after-cataract.

13. The composition according to claim 6, wherein the disease is cancer.

14. The composition according to claim 13, wherein the disease is lung cancer.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 1
gccaaagaag gacatgataa a        21

<210> SEQ ID NO 2
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 2
tggcaggtat ttgacatatt a        21

<210> SEQ ID NO 3
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 3
tctgatgatt tactagcaca a        21

<210> SEQ ID NO 4
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 4
atgtgaagct gcagctgtat a        21

<210> SEQ ID NO 5
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 5
agaaattcct gatccagaca a        21

<210> SEQ ID NO 6
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 6
gatccttctt tgactcatac a        21

<210> SEQ ID NO 7
<211> LENGTH: 21
<212> TYPE: DNA

```
<213> ORGANISM: Artificial Sequence
<220> FEATURE:
<223> OTHER INFORMATION: siRNA for inhibiting NF-kB p105 gene expression

<400> SEQUENCE: 7
gcctgaatca ttctcgattt a                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 8
ctacgttcct attgtcatta a                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 9
ggcttccttt cttggttcat a                                              21

<210> SEQ ID NO 10
<211> LENGTH: 21
<212> TYPE: DNA
<213> ORGANISM: Artificial Sequence
<220> FEATURE:
<223> OTHER INFORMATION: siRNA for inhibiting NF-kB p105 gene expression

<400> SEQUENCE: 10
tggttacaat cattgctgaa a                                              21
```